US008338638B2

(12) United States Patent
Achanath et al.

(10) Patent No.: US 8,338,638 B2
(45) Date of Patent: Dec. 25, 2012

(54) ANTIMICROBIAL DERIVATIVES OF ANACARDIC ACID AND PROCESS FOR PREPARING THE SAME

(75) Inventors: Radha Achanath, Bangalore (IN); Malladi Srinivas, Bangalore (IN); Candadal Seshadri Ramadoss, Bangalore (IN)

(73) Assignee: Unichem Laboratories Ltd., Mumbai (IN)

( * ) Notice: Subject to any disclaimer, the term of this patent is extended or adjusted under 35 U.S.C. 154(b) by 39 days.

(21) Appl. No.: 12/438,943

(22) PCT Filed: Aug. 24, 2007

(86) PCT No.: PCT/IN2007/000386
§ 371 (c)(1),
(2), (4) Date: Oct. 5, 2009

(87) PCT Pub. No.: WO2008/062436
PCT Pub. Date: May 29, 2008

(65) Prior Publication Data
US 2010/0016630 A1      Jan. 21, 2010

(30) Foreign Application Priority Data

Aug. 25, 2006   (IN) .......................... 1352/MUM/2006

(51) Int. Cl.
C07C 237/28    (2006.01)
C07C 65/01     (2006.01)
C07C 229/54    (2006.01)
A01N 37/18     (2006.01)

(52) U.S. Cl. ........ 562/437; 562/465; 562/474; 562/453; 514/568

(58) Field of Classification Search ........................ None
See application file for complete search history.

(56) References Cited

U.S. PATENT DOCUMENTS 2,433,388 A * 12/1947 Newbery ....................... 548/197
2,488,472 A * 11/1949 Kremers ........................ 568/780

FOREIGN PATENT DOCUMENTS

| JP | 06271502 A | * | 9/1994 |
| WO | WO 9530417 A1 | * | 11/1995 |
| WO | WO 2006042391 A2 | * | 4/2006 |

OTHER PUBLICATIONS

Kubo et al., Bioorg. Med. Chem. (1995) vol. 3(7) pp. 873-880.*
ElSholy et al, Journal of Medicinal Chemistry (1986), 29(5), 606-611.*
Bruce, Journal of Chemical Research, Synopses (1992)(7), pp. 224-225.*

* cited by examiner

*Primary Examiner* — Kamal Saeed
*Assistant Examiner* — Nyeemah A Grazier
(74) *Attorney, Agent, or Firm* — Harris Beach PLLC

(57) ABSTRACT

Derivatives of anacardic acid having antimicrobial properties and method for preparing said derivatives. The antimicrobial properties include bacteriostatic and bacteriocidal activity.

2 Claims, No Drawings

ANTIMICROBIAL DERIVATIVES OF ANACARDIC ACID AND PROCESS FOR PREPARING THE SAME

FIELD OF INVENTION

The invention discloses derivatives of anacardic acid having anti-microbial activity against microorganisms more specifically towards *Stapphalococcus aureus*, Methicillin resistant *Stapphalococcus aureus* (MRSA) and *Enterococcus fecalis* and process for preparing said derivatives.

BACKGROUND OF INVENTION

Anacardic acid is a non-isoprenoid long chain phenolic acid primarily obtained from the nut shells of the plant *Anacardium occidentale* native of South America.

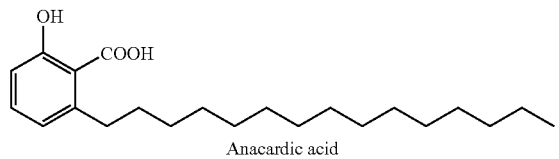

Anacardic acid

The solvent extracted cashewnut shell liquid (CNSL) is a rich source of many long chain phenolic compounds of which anacardic acids constitutes about 60-65% of the CNSL. The other major long chain constituents being cardol a dihydric component (15-20%) and cardanol a phenolic compound (10%).

The long aliphatic side chain of these phenolic constituents exists as a mixture of monoene, diene and triene, with the saturated component being present in negligible amount. Anacardic acids in CNSL exists as a mixture of monoene (38.4%), diene (17.4%) and triene (44.1%).

CNSL has for a long time being used as a raw material for the manufacture of polymers, paints, varnishes, brake linings etc. Apart from the industrial uses, the nut shell oil has also been used in the traditional medicine world wide for the treatment of inflammation, diarrhea, treatment of cracked foot etc.

Anacardic acid (6-pentadecyl salicylic acid) has been screened for various biological activities. It has been shown to be an inhibitor of lipoxygenase and xanthine oxidase. The antibacterial properties of anacardic acids has also been extensively studied by various groups. Kube et al studied the anti bacterial activity of the monoene ($C_{15:1}$), diene ($C_{15:2}$), triene($C_{15:3}$) and saturated ($C_{15:0}$) anacardic acids against *Stapphalococcus aureus* and Methicillin resistant *Stapphalococcus aureus*. They have shown that the triene ($C_{15:3}$) has a minimum inhibitory concentration (MIC) of 6.5 µg/mL while the saturated anacardic acid ($C_{15:0}$) has a MIC of 1600 µg/mL against MRSA. They have also studied the effect of the length of the side chain on the antibacterial activity and showed that the antibacterial activity was greater as the length of the alkyl chain increased.

Though a lot of study has been done to use the naturally occurring anacardic acids as such or in combination with known antibiotics to demonstrate the antimicrobial activity, there are no reports on the synthetic modifications of anacardic acids to enhance their antimicrobial activity.

Antibiotic resistance is a very serious problem in the hospitals and is growing at a rapid pace. Resistant strains have been isolated for almost all the existing antibiotics. With the growing problem of antimicrobial resistance there is a dire need for an effective molecule to combat this problem. The objective of this invention is to enhance the antimicrobial activity of saturated anacardic acid ($C_{15:0}$) especially against MRSA, by synthetic modifications.

SUMMARY OF THE INVENTION

The present invention discloses antimicrobial derivatives of anacardic acid and process for preparing said derivative.

The formula of said derivatives may be structurally represented as:

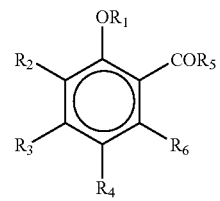

FORMULA I where $R_1$ comprises of H, $CH_3$, $C_2H_5$, $C_3H_7$ or Ac; $R_2$ is comprises of H, Br, F, Cl, I or $NH_2$, $NO_2$; $R_3$ comprises of H, Br, F, Cl, I or $NH_2$, $NO_2$; $R_4$ comprises of H, Br, or $NO_2$; $R_5$ comprises of H, $NH_2$, OH, $OCH_3$, $OC_2H_5$, $OC_3H_7$, OPh or NH—$R_7$ or O—$R_7$; and $R_7$ comprises of a cyclic hydrocarbon or its derivatives including but not limited to:

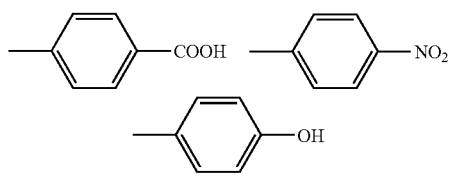

$R_6$ may be an alkyl chain having a length of $C_1$ to $C_{20}$, the chain being either totally saturated or having one or more unsaturations. $R_6$ may also be an unsaturated alkyl chain comprising an aldehyde functional group where the aldehyde may be coupled to any of the amino acids or organic acids or antibiotics.

The invention particularly provides for process for preparation of 6-Pentadecyl-2-acetyloxybenzoic acid, 3,5-Dinitro-6-pentadecyl-2-hydroxybenzoic, 3,4-Dinitro-6-pentadecyl-2-hydroxybenzoic, 3,5-Dinitro-6-pentadecyl-2-acetyloxybenzoic, 3,4-Dinitro-6-pentadecyl-2-acetyloxybenzoic acid, 5-bromo-6-pentadecyl-2-hydroxybenzoic acid, 3-nitro-6-pentadecyl-2-hydroxybenzoic acid, 3-nitro-6-pentadecyl-2-acetyloxybenzoic acid, 5-nitro-6-pentadecyl-2-hydroxybenzoic acid, 5-nitro-6-pentadecyl-2-acetyloxybenzoic acid, 4-nitro-6-pentadecyl-2-hydroxybenzoic acid, 4-nitro-6-pentadecyl-2-acetyloxybenzoic acid and their use for preventing the growth of microorganisms including gram-negative or gram positive microorganisms such as *Stapphalococcus aureus*, and Methicillin resistant *Stapphalococcus aureus* etc.

DETAILED DESCRIPTION OF THE INVENTION

The invention specifically relates to the process for the preparation of antimicrobial derivatives of saturated anacardic acid ($C_{15:0}$). The mixture of anacardic acids chromatographically purified from CNSL was hydrogenated using Pd—C to get the saturated anacardic acid ($C_{15:0}$). Said derivatives were prepared by adopting the techniques used in synthetic chemistry for nitration, halogenation and acetylation of various organic compounds. The synthesized derivatives were assayed for anti bacterial activity against *Stapphalococcus aureus* and Methicillin resistant *Stapphalococcus aureus* and *Enterococcus fecalis* by the broth assay used for antibiotic susceptibility tests and the minimum inhibitory concentration (MIC) and minimum bactericidal concentration (MBC) determined. The derivatives showed a MIC of 1-10 μg/mL and MBC of 2-10 μg/mL against MRSA and *Stapphalococcus aures*. A few of the derivatives showed a MBC of 2 μg/mL and MIC of 1 μg/mL.

The activity of seventeen different derivatives of anancardic acid have been tested against the three bacteria namely *Stapphalococcus aureus* and Methicillin resistant *Stapphalococcus aureus* and *Enterococcus fecalis* and compared with anancardic acid. The results of said comparative study have been shown in Table and clearly indicate the high efficacy of the derivatives.

vacuum for 2 hrs. The yield obtained was 4.6 g (83%) and the product had a melting point of 62-68° C. Mass [M$^+$] m/z: 389. IR (KBr) $v_{max}$/cm$^{-1}$: 2922, 2850, 1764, 1698, 1606, 1465, 1370, 1314, 1222. $^1$H NMR (CDCl$_3$, 400 MHz) δ: 0.893-0.86δ (3H, t); 1312-1.244δ (24H, s); 1.626(2H, m); 2.291 (3H, s); 2.80-2.76(2H, t); 6.93-7.00(1H, d; 7.15-7.17(1H, d); 7.38-7.4(1H, t).

FORMULA II: AAA

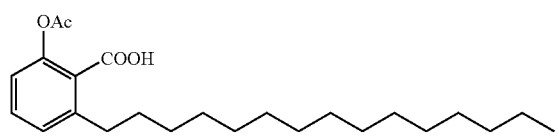

TABLE 1

Antibacterial activity of the derivatives:

| S. No | Sample | ID | MRSA | | Sa (NCTC8325) | | E. fecalis | |
|---|---|---|---|---|---|---|---|---|
| | | | MIC (μg/ml) | MBC (μg/ml) | MIC (μg/ml) | MBC (μg/ml) | MIC (μg/ml) | MBC (μg/ml) |
| 1 | MDBAA | UC-AA-911 | 0.5 | 4 | 3-5 | 5 | 1 | 3 |
| 2 | MAA | UC-AA-908 | 1 | 4 | 1 | 8 | 1 | 6 |
| 3 | MDAA | UC-AA-915 | 2 | 4 | 6 | 8 | 0.5 | 2 |
| 4 | DAA | UC-AA-903 | 3 | 6 | 2 | 3-5 | 6 | 6 |
| 5 | AAA | UC-AA-902 | 2 | 6 | 6 | 7-8 | 1 | 6 |
| 6 | ADAA | UC-AA-905 | 4 | 10 | 2 | 6 | 6 | 6 |
| 7 | NAA | UC-AA-904 | 1 | 10 | 1 | 7-8 | 0.5 | 7 |
| 8 | MAAY | UC-AA-919 | 2 | 10 | 3-5 | >10 | 6 | >10 |
| 9 | ANAA | UC-AA-906 | 2 | >10 | 1 | >10 | 0.5 | 7 |
| 10 | ADBAA | UC-AA-912 | 9-10 | >10 | >10 | >10 | 1 | 3 |
| 11 | MAA-APA | UC-AA-909 | 10-20 | >20 | >10 | >10 | 6 | >10 |
| 12 | MAA-PABA | UC-AA-910 | >20 | >20 | >10 | >10 | 6 | >10 |
| 13 | MAA-Ba | UC-AA-913 | >20 | >20 | >10 | >10 | 6 | >10 |
| 14 | MAA-F | UC-AA-914 | >20 | >20 | >10 | >10 | 6 | >10 |
| 15 | MAA-PNA | UC-AA-916 | >20 | >20 | >10 | >10 | >10 | >10 |
| 16 | MAA-PAA | UC-AA-917 | >20 | >20 | >10 | >10 | >10 | >10 |
| 17 | DBAA | UC-AA-907 | >20 | >20 | >10 | >10 | 6 | 6 |
| 18 | AA | UC-AA-901 | >50 | >50 | >10 | >10 | 0.5 | 6 |

The preferred embodiments of the inventions are herewith described with respect to the following examples:

EXAMPLE-1

Preparation of 6-Pentadecyl-2-acetyloxybenzoic acid (AAA)

A solution of AA (5 g, 0.014 mmol) in pyridine (35 ml) was treated with acetic anhydride (5 ml) at room temperature. Resulting mixture was stirred at room temperature for 6 hrs. Acidified the reaction mixture to pH=2 using dilute HCl. The product that precipitated out was extracted into ethyl acetate. Washed the ethyl acetate layer with water (25 ml×3). Evaporated solvent under reduced pressure to obtain crude product (5.5 g). The crude product obtained was triturated with chilled hexane (5 ml×2) to obtain a solid. Filtered and washed the solid with cold hexane. Finally dried the material under

EXAMPLE-2

Preparation of 3,5-Dinitro-6-pentadecyl-2-hydroxybenzoic acid (DAA)

A suspension of anacardic acid (200 mg, 0.574 mmol) in conc. H$_2$SO$_4$ (8 ml) was cooled to 0° C. To the cold mixture, conc. HNO$_3$ (2 ml, 69% solution) was added slowly maintaining the temperature below 5° C. The reaction mixture was stirred at 5° C. for 15 min and poured into crushed ice. The product precipitated out and was extracted into ethyl acetate (25 ml×2). The ethyl acetate layer was washed with water (25 ml×4) and dried over anhydrous Na$_2$SO$_4$. Finally the solvent was evaporated under reduced pressure. The crude product was purified by silica gel column chromatography using Hexane-ethyl acetate solvent system. The pure product obtained after concentration (oily) was triturated with hexane (5 ml) to obtain a solid. The product was separated by centrifugation, washed with hexane (1 ml) and dried under vacuum. The yield obtained was 80% (204 mg). The product had a melting point of 78-82° C. and has structural formula III. Mass [M$^+$] m/z 437. IR (KBr) $v_{max}$/cm$^{-1}$: 3098, 2923, 2851, 1715, 1601, 1551, 1444, 1340, 1278, 1168, 1040. $^1$H NMR (CDCl$_3$, 400 MHz) δ: 0.893-0.86δ (3H, t); 1.244δ (22H, s); 1.41δ (2H, m); 1.65δ (2H, m); 3.01-2.9δ (2H, t); 8.87δ (1H, s).

FORMULA III: DAA

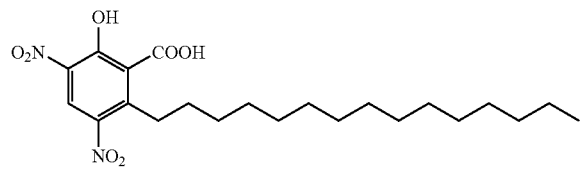

EXAMPLE-3

Preparation of
3,4-Dinitro-6-pentadecyl-2-hydroxybenzoic acid
(NAA)

To a suspension of anacaridic acid (200 mg, 0.574 mmol) in conc. H$_2$SO$_4$ (4 ml), conc. HNO$_3$ (2 ml, 69% solution) was added dropwise over a period of 5 min at room temperature. During the addition of nitric acid, the temperature of the reaction mixture raised to about 40-45° C. The mixture was stirred for 15 min and poured into crushed ice. The product precipitated out and was extracted into ethyl acetate (25 ml×2). The ethyl acetate layer was washed with water (25 ml×4) and dried over anhydrous. Na$_2$SO$_4$. Finally the solvent was evaporated under reduced pressure to obtain the crude product. The crude product was purified by silica gel column chromatography. The mobile phase used was hexane-ethylacetate system. The yield obtained was 52% (132 mg). The product obtained after column chromatography was treated with 5 ml of 1:1 mixture of DCM/hexane to obtain a solid. The product was separated by centrifugation, washed with hexane and dried under vacuum. The over all yield obtained was 32% (80 mg). The product was found to decompose at 75-80° C. and has structural formula IV. Mass [M$^+$] m/z: 438. IR (KBr) $v_{max}$/cm$^{-1}$: 3264, 2917, 2840, 1633, 1589, 1541, 1445, 1353, 1165, 1053, 919. $^1$H NMR (CDCl$_3$, 400 MHz) δ: 0.893-0.86δ (3H, t); 1.255δ (22H, s); 1.34δ (2H, m); 1.62-1.6δ (2H, m); 2.91-2.87δ (2H, t); 8.96δ (1H, s).

FORMULA IV: NAA

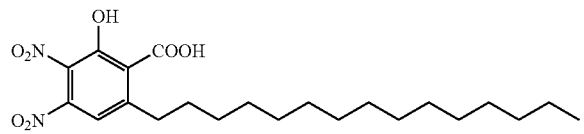

EXAMPLE-4

Preparation of
3,5-Dinitro-6-pentadecyl-2-acetyloxybenzoic acid
(ADAA)

A mixture of DAA obtained in Example-2 (80 mg, 0.23 mmol) and acetyl chloride (5 ml) was refluxed for 7 hrs. The reaction mixture was poured into icecold water. The product precipitated out and was extracted into ethyl acetate (25 ml×2), washed with water (25 ml×4) and dried over anhydrous Na$_2$SO$_4$. The solvent was evaporated under reduced pressure. The residue obtained was triturated with hexane (3 ml) to obtain a solid. The product was separated by centrifugation, washed with hexane and dried under vacuum. The yield obtained was 52% (46 mg). The product was found to melt at 55-57° C., with decomposition and has structural formula V. Mass [M$^+$] m/z: 479. IR (KBr) $v_{max}$/cm$^{-1}$: 3098, 2917, 2850, 1717, 1599, 1542, 1449, 1344, 1268, 1162, 1042. $^1$H NMR (CDCl$_3$, 400 MHz) d: 0.883-0.856δ (3H, t); 1.24δ (22H, s); 1.41-1.39δ (2H, m); 1.67-1.63δ (2H, m); 2;291δ (3H, s); 2.99δ (2H, t); 8.87δ (1H, d); 7.67-7.65δ (1H, s).

FORMULA V: ADAA

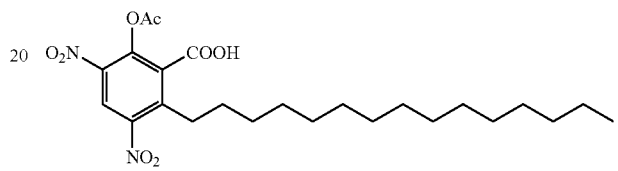

EXAMPLE-5

Preparation of
3,4-Dinitro-6-pentadecyl-2-acetyloxybenzoic acid
(ANAA)

A mixture of NAA obtained in Example-3 (25 mg, 0.057 mmol) and acetyl chloride (2 ml) was refluxed for 7 hrs. The reaction mixture was poured into icecold water. The product precipitated out and was extracted into ethyl acetate (15 ml×2). The ethyl acetate layer was washed with water (15 ml×4) and dried over anhydrous Na$_2$SO$_4$. The solvent was evaporated under reduced pressure. The residue obtained was triturated with hexane (3 ml) to obtain a solid. The product was separated by centrifugation, washed with hexane and dried under vacuum for 2 hrs. The yield obtained was 51% (14 mg) and has structural formula VI. Mass [M$^+$] m/z: 479. IR (KBr) $v_{max}$/cm$^{-1}$: 3110, 2916, 2849, 1807, 1595, 1539, 1372, 1349, 1152, 1045. $^1$H NMR (CDCl$_3$, 400 MHz) d: 0.89-0.859δ (3H, t); 1.392-1.025δ (24H, s); 1.61-1.656δ (2H, m); 2.413δ (3H, s); 2.85δ (2H, t); 8.862δ (1H, d).

FORMULA VI: ANAA

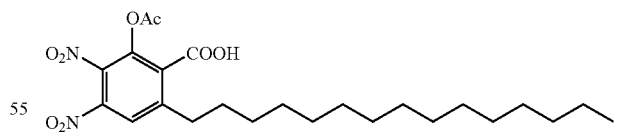

EXAMPLE-6

Preparation of
5-Bromo-6-pentadecyl-2-hydroxybenzoic acid
(DBAA)

To a solution of anacardic acid (1 g, 2.87 mmol) in DCM (30 ml), a solution of bromine (300 μl) in DCM (1 ml) was added dropwise at room temperature over a period of 10 min.

The reaction mixture was stirred at room temperature for 30 min. The mixture was then washed with water (25 ml×3) and dried over anhydrous $Na_2SO_4$. Evaporated solvent under reduced to obtain crude product.

The crude product obtained was triturated with hexane to obtain a solid. The product was separated by filtration, washed the solid with hexane and dried under vacuum for 2 hrs. The yield obtained was 56% (685 mg).

The product had a melting point of 70-75° C. and has structural formula VII. Mass [M$^+$] m/z: 425. IR (KBr) $v_{max}$/cm$^{-1}$: 3075, 2917, 2949, 1650, 1590, 1448, 1282, 1219, 893, 829, 722. $^1$H NMR (CDCl$_3$, 400 MHz) δ: 0.893-0.86δ (3H, t); 1.253δ (22H, s); 1.44-1.42δ (2H, m); 1.59δ (2H, m); 3.15-3.115δ (2H, t); 6.79-6.77δ (1H, d); 7.65-7.63δ (1H, d); 10.8δ (1H, s).

FORMULA VII: DBAA

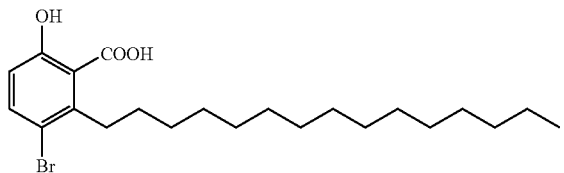

EXAMPLE-7

Preparation of
5-Bromo-6-pentadecyl-2-acetyloxybenzoic acid
(ABAA)

A solution of 5-Bromo-6-pentadecyl-2-hydroxybenzoic acid in DCM (15 ml) was treated with pyridine (500 μl) followed by acetic anhydride (50 μl). Resulting mixture was stirred at room temperature for 16 hrs. Acidified the reaction mixture to pH=2 using dilute HCl. Separated the organic layer and washed with water (10 ml×3). Evaporated solvent under reduced pressure to obtain crude product. The crude product obtained was triturated with hexane to obtain a solid. Filtered and washed the solid with hexane. Finally dried the material under vacuum for 2 hrs. The yield obtained was 46% (100 mg) and the product had a melting point of 65-67° C. Mass [M$^+$] m/z: 467. IR (KBr) $v_{max}$/cm$^{-1}$:2918, 2850, 1784, 1697, 1590, 1467, 1387, 1275, 1185, 880. $^1$H NMR (CDCl$_3$, 400 MHz) □: 0.893-0.86δ (3H, t); 1.25δ (22H, s); 1.394-1.362δ (2H, m); 1.65-1.59δ (2H, m); 2.291δ (3H, s); 2.86-2.81δ (2H, t); 6.93-6.91δ (1H, d); 7.67-7.65δ (1H, d).

FORMULA V: ABAA

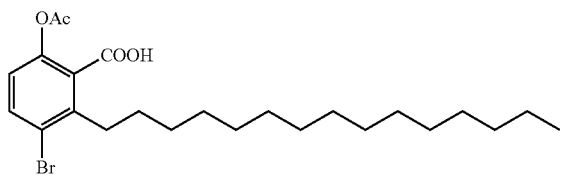

EXAMPLE-8

Preparation of 2-Methoxy-6-Pentadecyl-benzoic acid (MAA)

A solution of AA (10 g, 0.0287 mmol) in acetone (100 ml) was treated with anhydrous $K_2CO_3$ (10 g, 0.0723 mmol) followed by dimethyl sulphate (15 ml, 0.1575 mmol). The mixture was stirred under refluxed condition for 4 hrs. Evaporated solvent to dryness under reduced pressure. The residue obtained was dissolved in ethylacetate (100 ml) and washed with water (50 ml×2). Evaporated solvent under reduced pressure to obtain an oily material. The product obtained was refluxed with a mixture of KOH/BuOH/H$_2$O (30 g, 0.535 mmol; 50 ml; 20 ml) for 2 hrs. Cooled the reaction mixture to room temperature and acidified to a pH=2 using dil HCl. Separated the organic layer and washed with water (50 ml×2). Evaporated solvent under reduced pressure to obtain crude product. The crude product obtained was triturated with hexane to obtain a solid. The product was filtered, washed with hexane and dried under vacuum for 2 hrs. The yield obtained was 98% (10.6 g). The product had a melting point of 65-72° C. and has structural formula IX Mass [M$^+$] m/z: 361. IR (KBr) $v_{max}$/cm$^{-1}$: 3249, 2920, 2850, 1709, 1586, 1472, 1390, 1247, 1077. $^1$H NMR (CDCl$_3$, 400 MHz) δ: 0.896-0.863δ (3H,t); 1.31-1.24δ (24H, s); 1.63δ (2H, m); 2.74-2.7δ (2H, t); 3.89δ(3H, s) 6.821-6.8δ (1H, d); 6.8-6.86δ (1H, d); 7.33-7.29δ (1H, t).

FORMULA IX: MAA

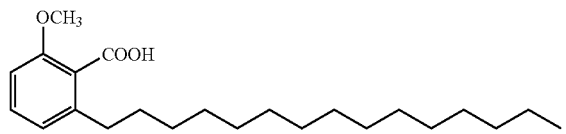

EXAMPLE-9

Preparation of
5Bromo-6-pentadecyl-2-methoxybenzoic acid
(MDBAA)

A solution of MAA (300 mg, 0.83 mmol) in DCM (10 ml) was treated with a solution of bromine (90 μl) in DCM (5 ml). Resulting mixture was stirred at room temperature for 30 min. The mixture was washed with water, dried over anhy. Na$_2$SO$_4$ and the solvent evaporated under reduce pressure to obtain the crude product. The product obtained was then triturated with acetonitrile to obtain 300 mg (70%) of pure product The product had a melting point of 65-68° C. and has structural formula X. Mass [M$^+$] m/z: 437. IR (KBr) $v_{max}$/cm$^{-1}$: 3086, 2918, 2849, 1711, 1577, 1464, 1432, 1391, 1275, 1094, 802, 723. $^1$H NMR (CDCl$_3$, 400 MHz) δ: 0.89-0.86δ (3H, t); 1.4-1.24δ (24H, s); 1.64-1.605δ (2H, m); 2.77-2.729δ (2H, t); 3.858δ (3H, s); 6.71-6.68δ (1H, d); 7.55-7.53δ (1H, d).

FORMULA X: MDBAA

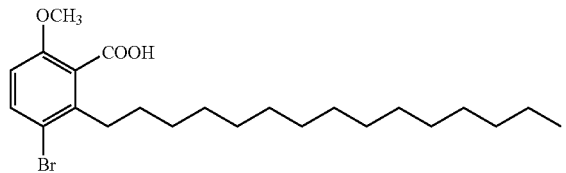

EXAMPLE-10

Preparation of 3,5-Dinitro-6-pentadecyl-2-Methoxybenzoic acid (MDAA)

A suspension of Methoxy anacardic acid (800 mg, 2.21 mmol) in Conc. $H_2SO_4$ (10 ml) was treated with Conc. $HNO_3$ (3 ml, 69% solution) at room temperature. The reaction mixture was stirred at the same temperature for 15 min. Then poured the mixture into crushed ice. The product that precipitated out was extracted into ethyl acetate (25 ml×2). Washed the ethyl acetate layer with water (25 ml×4). Dried the ethyl acetate layer over anhy. $Na_2SO_4$. Finally evaporated the solvent under reduced pressure to obtain the crude product. The crude product was purified by column chromatography using silica gel. The mobile phase used was 100% $CHCl_3$. The yield obtained was 72% (650 mg). The product had a melting point of 68-75° C. and has structural formula XI. Mass [M⁺] m/z: 451. IR (KBr) $v_{max}/cm^{-1}$: 2918, 1709, 1592, 1536, 1470, 1343, 1273, 1055. $^1$H NMR (CDCl$_3$, 400 MHz) δ: 0.769-0.735δ (3H, t); 1.27-1.17δ (22H, s); 1.54-1.505δ (2H, m); 2.8-2.76δ (2H, m); 3.9δ (3H, s); 8.4δ (1H, s).

FORMULA XI: MDAA

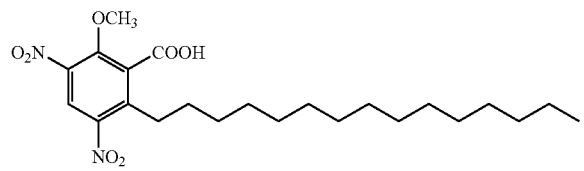

EXAMPLE-11

Coupling between 2-Methoxy-6-Pentadecyl-benzoic acid and (+)-6-aminopencillanic acid (MAA-APA)

A solution of MAA (500 mg, 1.38 mmol) in DCM (5 ml) was treated with thionyl chloride (1 ml) for 1 hrs. Removed the excess thionyl chloride and traces of solvent under reduced pressure. The resulting residue was dissolved in DCM and added dropwise to a cold (maintained at 10° C.) suspension of 6-APA in DCM/TEA (5 ml/1 ml), over a period of 10 min. The resulting mixture was stirred at room temperature for 2 hrs. Acidified the reaction mixture with a solution citric acid to pH=4. Then separated the organic layer, washed the organic layer with water and evaporated solvent to dryness. The residue obtained was redissolved in ACN and treated with aqueous $NaHCO_3$ (120 mg). Resulting mixture was stirred for 30 min. at room temperature and then concentrated under reduced pressure to obtain the sodium salt of the APA derivative. The solid obtained was washed with hexane and finally dried under vacuum for 1 hr. The yield obtained was 75% (600 mg) and has structural formula XII, Mass [M⁺] m/z: 557. IR (KBr) $v_{max}/cm^{-1}$: 3413, 2923, 2852, 1723, 1648, 1599, 1587, 1468, 1401, 1260, 1078. $^1$H NMR (CDCl$_3$, 400 MHz) δ: 0.898-0.857δ (3H, t); 1.25-1.21δ (24H, s); 1.62δ (2H, m); 2,71-2.68δ (2H, m); 3.87-3.83δ (3H, s); 6.81-6.79δ (1H, d); 6.9-6.88δ (1H, d); 7.32-7.26δ (1H, t); 7.75-7.73δ (1H, d), 8.13-8.114δ (1H, d)

FORMULA XII: MAA-APA

EXAMPLE-12

Coupling between 2-Methoxy-6-Pentadecyl-benzoic acid and p-Amino benzoic acid (MAA-PABA)

A solution of MAA (500 mg, 1.38 mmol) in DCM (5 ml) was treated with thionyl chloride (1 ml) for 1 hrs. Removed the excess thionyl chloride and traces of solvent under reduced pressure. The resulting residue was dissolved in DCM (5 ml) and added dropwise to a cold (maintained at 10° C.) suspension of PABA in DCM/TEA (5 ml/350 µl), over a period of 10 min. The resulting mixture was stirred at room temperature for 16 hrs. Acidified the reaction mixture with with dil HCl to pH=2. Then separated the organic layer, washed the organic layer with water and evaporated solvent to dryness. The residue obtained was triturated with ACN. The solid obtained was filtered and washed with ACN.

The yield obtained was 40% (260 mg). The product had a melting point of 189-192° C. and has structural formula XIII. Mass [M⁺] m/z: 482. IR (KBr) $v_{max}/cm^{-1}$: 3289, −2923, 2852, 1686, 1595, 1540, 1470, 1418, 1406, 1266, 1174, 1076, 775. $^1$H NMR (CDCl$_3$, 400 MHz) δ: 0.888-0.857δ (3H, t); 1.25-1.21δ (24H, s); 1.62δ (2H, m); 2.71-2.68δ (2H, m); 3.87-3.83δ (3H, s); 6.81-6.79δ (1H, d); 6.9-6.88δ (1H, d); 7.32-7.26δ (1H, t); 7.75-7.73δ (1H, d); 8.13-8.114δ (1H, d)

FORMULA XIII: MAA-PABA

EXAMPLE-13

Coupling between 2-Methoxy-6-Pentadecyl-benzoic acid and L-Phenylalanine (MAA-F)

A solution of MAA (50 mg, 0.138 mmol) in DCM (5 ml) was treated with thionyl chloride (1 ml) for 1 hrs. Removed the excess thionyl chloride and traces of solvent under reduced pressure. The resulting residue was dissolved in DCM (5 ml) and added dropwise to a cold (maintained at 10° C.) suspension of Phe in DCM/TEA (5 ml/35 µl), over a period of 10 min. The resulting mixture was stirred at room temperature for 16 hrs. Acidified the reaction mixture with dil HCl to pH=2. Separated the organic layer, washed the organic layer with water and evaporated solvent to dryness. The residue obtained was purified by column using $SiO_2$ as the stationary phase and 100% EA as the mobile phase. The yield obtained was 54% (38 mg) and has structural formula XIV.

Mass [M⁺] m/z: 509. IR (KBr) $v_{max}$/cm⁻¹: 3545, 3331, 2920, 2849, 1766, 1731, 1648, 1505, 1467, 1259.

FORMULA XIV: MAA-F

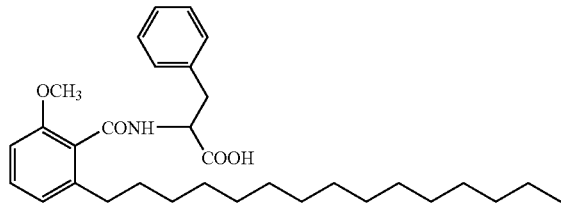

EXAMPLE-14

Coupling between 2-Methoxy-6-Pentadecyl-benzoic acid and Bakuchiol (MAA-Ba)

A solution of MAA (315 mg) and bakuchiol (220 mg) in DCM (5 ml) was treated with DCC (190 mg, 0.922 mmol) followed by DMAP (1 mg). Resulting mixture was stirred at room temperature for 2 hrs. Evaporated solvent and the residue obtained was loaded on a $SiO_2$ column and eluted with 100% $CHCl_3$ to obtained the pure product (an oil). The yield obtained was 100 mg. The structural formula may be represented as formula XV. Mass [M⁺] m/z: 598.

FORMULA XV: MAA-Ba

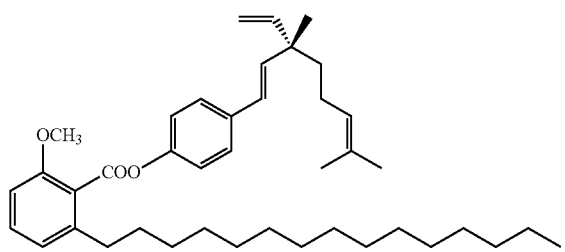

EXAMPLE-15

Coupling between 2-Methoxy-6-Pentadecyl-benzoic acid and L-Thyrosine (MAAY)

A solution of MAA (50 mg, 0.138 mmol) in DCM (2 ml) was treated with thionyl chloride (100 μl) for 1 hrs. Removed the excess thionyl chloride and traces of solvent under reduced pressure. The resulting residue was redissolved in DCM (5 ml) and added dropwise to a cold (maintained at 10° C.) suspension of Tyr in DCM/TEA (5 ml/35 μl), over a period of 10 min. The resulting mixture was stirred at room temperature for 16 hrs. Acidified the reaction mixture with dil HCl to pH=2. Separated the organic layer, washed the organic layer with water and evaporated solvent to obtain crude product. The crude yield obtained was 71% (52 mg). The structural formula may be represented as formula XVI. Mass [M⁺] m/z: 520

FORMULA XVI: MAAY

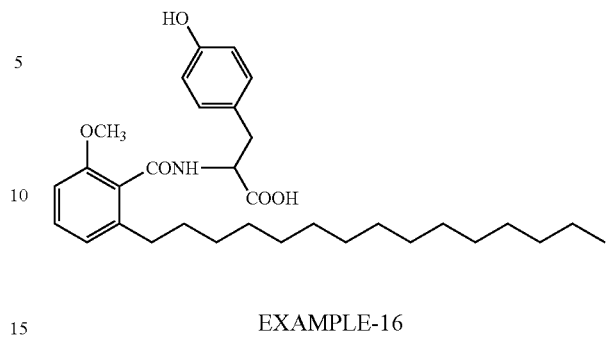

EXAMPLE-16

Coupling between 2-Methoxy-6-Pentadecyl-benzoic acid and p-Nitro aniline (MAA-PNA)

A solution of MAA (200 mg, 0.552 mmol) in DCM (5 ml) was treated with thionyl chloride (0.5 ml) for 1 hrs. Removed the excess thionyl chloride and faces of solvent under reduced pressure. The resulting residue was dissolved in DCM (5 ml) and added dropwise to a cold (maintained at 10° C.) suspension of PNA in DCM/TEA mixture (5 ml/150 μl), over a period of 10 min. The resulting mixture was stirred at room temperature for 3 hrs. Acidified the reaction mixture with dil HCl to pH=2. Separated the organic layer, washed the organic layer with water and evaporated solvent to dryness. Triturated the crude product with hexane and then with ACN to obtain a pure product. The yield obtained was 54% (38 mg). The product was found to melt at 103-105° C., with decomposition. The structural formula may be represented as formula XVII. Mass [M⁺] m/z: 481. IR (KBr) $v_{max}$/cm⁻¹: 3649, 2920, 2850, 1661, 1556, 1507, 1333, 1271, 1110, 750. ¹H NMR ($CDCl_3$, 400 MHz) δ:

FORMULA XVII: MAA-PNA

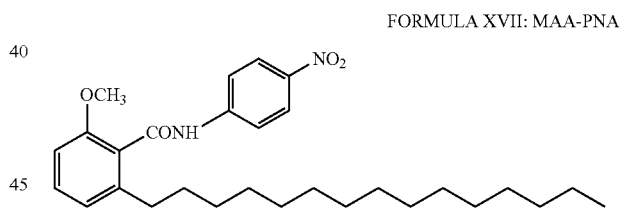

Procedure for Antimicrobial Testing:

The bacterial colonies from Luria-Bertani (LB) agar plates were inoculated into sterile LB broth and incubated in an incubator shaker for 12 h. This culture was diluted such that the innoculum when added to the test broth would correspond to $10^5$ colony forming units (CFU). The broth assays were done in sterile culture tubes containing 5 mL of LB medium. The test compounds dissolved in ethanol and controls were added to these tubes and then the innoculum was added and the tubes incubated at 37° C. for 24 h. After 24 h incubation the $OD_{600}$ was recorded and then plated on LB agar plates and incubated fore 24 h at 37° C. The colonies were counted and the minimum inhibitory concentration (MIC) and minimum bactericidal concentration (MBC) calculated. The MIC is determined by the minimum concentration of the sample at which no growth was observed as determined by measuring the $OD_{600}$. The MBC is determined by the concentration at which there is a reduction in the cfu in the broth assay from $10^5$ to $10^3$ counted after plating on LB agar plates. The results are tabulated in Table-1

While the present invention has been described with respect to certain preferred embodiments, it will be apparent to those skilled in the art that various changes and modifications may be made without departing from the scope of the invention as defined in the following claims.

We claim:

1. An antimicrobial derivative of anacardic acid of formula (I),

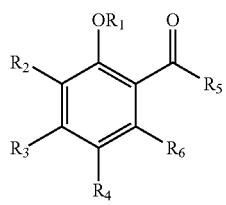

wherein $R_1$ is H, C(O)CH$_3$ or CH$_3$; $R_2$ is NO$_2$ or H; $R_3$ is NO$_2$ or H; $R_4$ is NO$_2$, H or Br; $R_5$ is OH or CH—R$_7$, where $R_7$ is C$_6$H$_5$COOH; and $R_6$ is C$_1$-C$_{20}$ alkyl chain, wherein the derivative has a formula selected from the group consisting of:

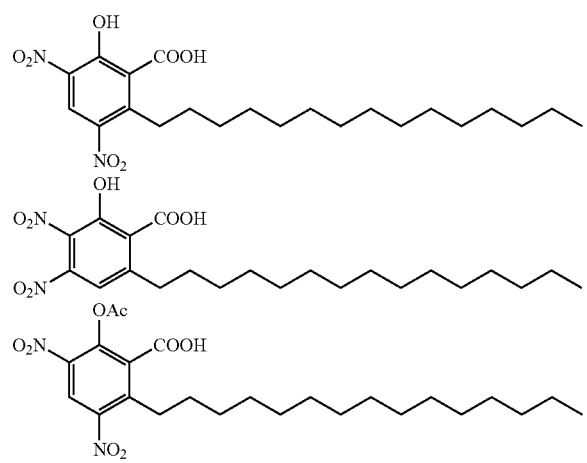

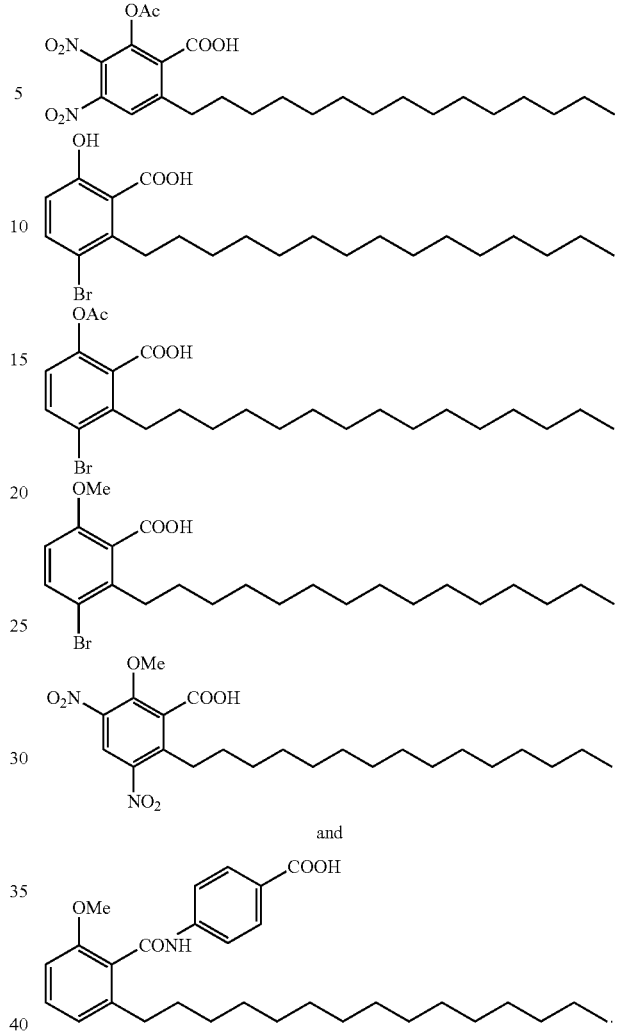

2. A composition comprising the antimicrobial derivative of anacardic acid of claim 1 and an amino acid, an organic acid or an antibiotic

* * * * *